United States Patent [19]
Martin

[11] 3,999,550
[45] Dec. 28, 1976

[54] EXTERNAL MALE CATHETER

[76] Inventor: Burnidine E. Martin, 601 S. 15th, Worland, Wyo. 82401

[22] Filed: Apr. 5, 1976

[21] Appl. No.: 673,417

[52] U.S. Cl. ............................................... 128/295
[51] Int. Cl.[2] .......................................... A61F 5/44
[58] Field of Search ....... 128/294, 295, 2 F, 132 R, 128/283; 4/110

[56] References Cited
UNITED STATES PATENTS

| | | | |
|---|---|---|---|
| 3,032,038 | 5/1962 | Swinn | 128/295 |
| 3,043,306 | 7/1962 | Hergatt et al. | 128/283 |
| 3,405,715 | 10/1968 | Moss | 128/295 |

FOREIGN PATENTS OR APPLICATIONS

| | | | |
|---|---|---|---|
| 674,158 | 4/1939 | Germany | 128/295 |
| 994,274 | 6/1965 | United Kingdom | 128/295 |

*Primary Examiner*—Robert W. Michell
*Assistant Examiner*—Henry S. Layton
*Attorney, Agent, or Firm*—Mason, Fenwick & Lawrence

[57] ABSTRACT

An external male catheter device including a flexible external catheter tube adapted for application to the male organ to transmit urine voided by the patient, a cylindrical shaped belt receptacle over which the base of the catheter tube extends, support straps which extend around the body of the patient, said support straps have free ends which extend into a cup recess around the belt receptacle and are retained in position by a belt retaining ring which surrounds the catheter tube and presses against the belt receptacle to retain the catheter tube and support straps in the desired position.

6 Claims, 4 Drawing Figures

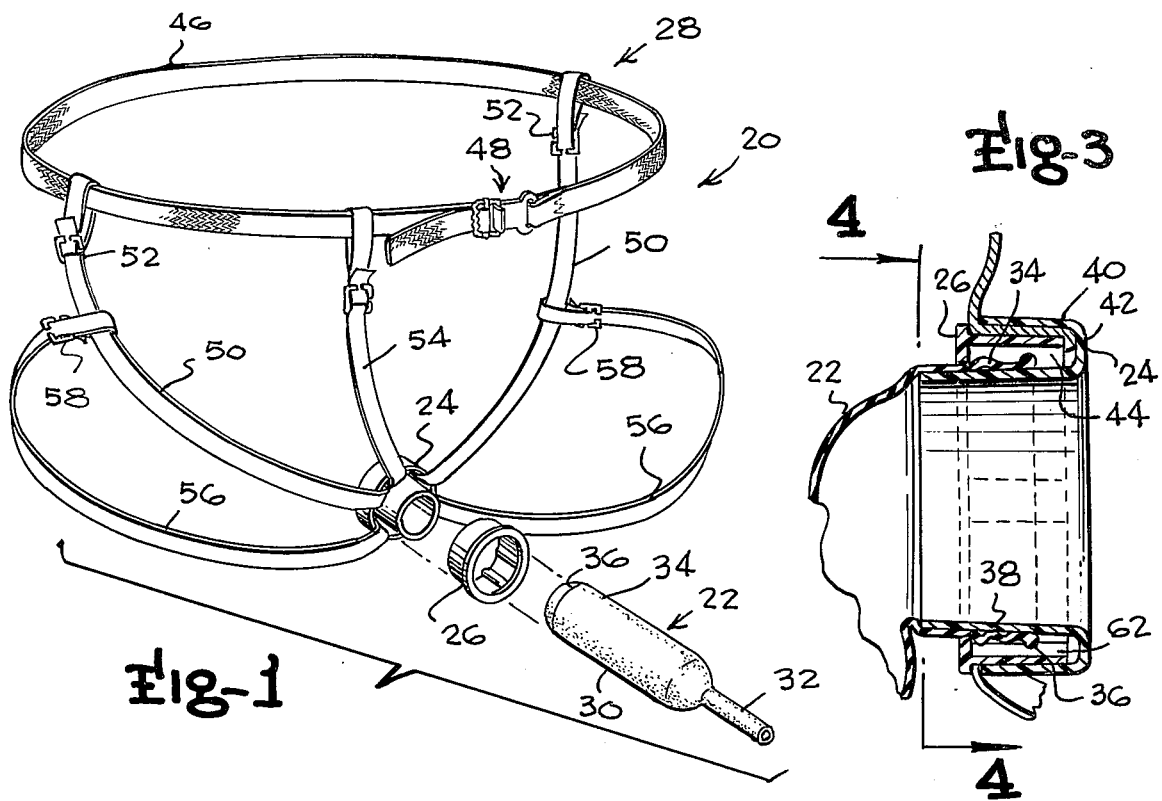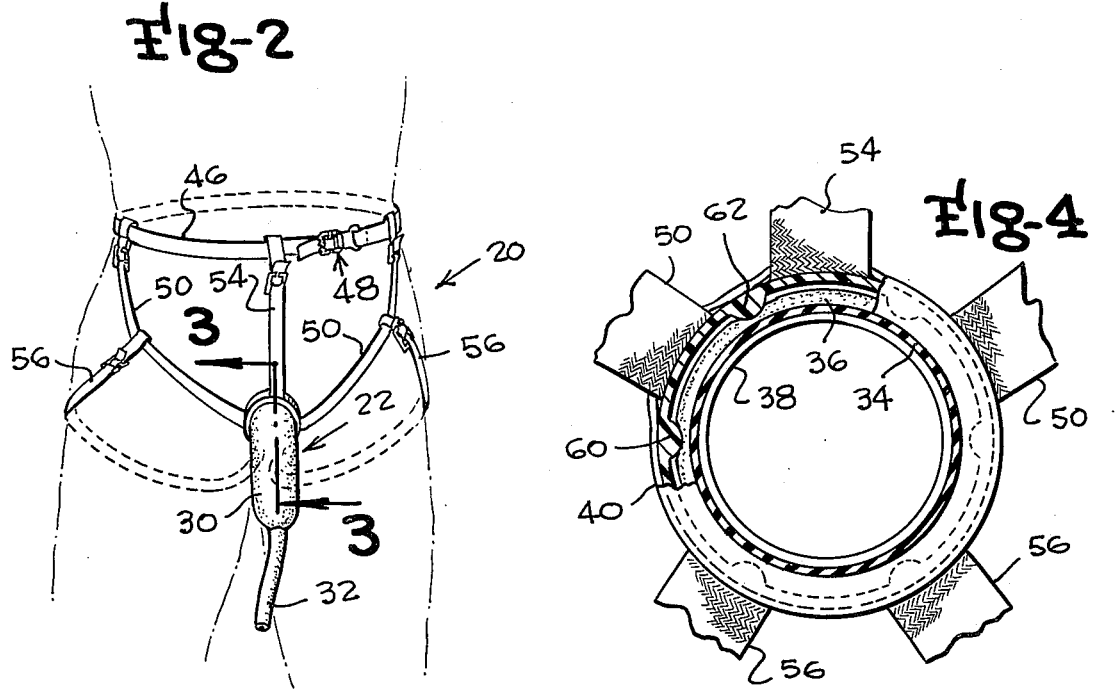

EXTERNAL MALE CATHETER

This device relates to a disposable external male catheter device and more particularly to a device for transmitting urine voided by an incontinent male patient.

Previous male incontinence devices have disclosed flexible catheter tubes to enclose the male organ with the catheter tube being held in position by straps or bands which extend around portions of the patient's body. These previous devices have, however, not been easy to position on the patient and to adjust to the desired position nor have these devices been simple to remove from the patient and disassemble for cleaning. These previous devices have sometimes caused external infection even though the external type catheters are very desirable because they eliminate the requirement for irrigating the patient's urinary tract as is necessary with the internal type catheter devices thereby avoiding the potential infections which are an inherent possibility with the internal type catheters. Many of the known devices have required the skill of a registered nurse to position and adjust to avoid serious complications.

It is, therefore, a primary object of the present invention to provide a new and improved external male catheter.

It is an additional object of the present invention to provide an external male catheter which is simple to position and adjust without requiring the skill and knowledge of a registered nurse.

It is a further object of the present invention to provide an external male catheter which is quickly and easily disassembled to permit cleaning and inspection.

An additional object of the present invention is to provide an external male catheter which prevents infection and provides a high degree of freedom for the patient.

Another object of the present invention is to provide an external male catheter which is light weight, comfortable and inexpensive.

Other objects and advantages of the invention will become more apparent to those persons having ordinary skill in the art to which the invention pertains, from the following decription taken in conjunction with the accompanying drawings wherein:

FIG. 1 is an exploded perspective view of an embodiment of the present invention;

FIG. 2 is a front view of the embodiment, illustrated in FIG. 1, positioned on the body of a patient;

FIG. 3 is an enlarged cross sectional view taken along lines 3—3 in FIG. 2; and

FIG. 4 is a cross sectional view taken along line 4—4 in FIG. 3.

Referring to the drawings, particularly in FIGS. 1 and 2, there is illustrated an external catheter device 20, embodying the invention which may be mounted on the patient's body as shown in FIG. 2. The device generally includes a flexible catheter tube 22, a cylindrical belt receptacle 24, a belt retaining ring 26 and a support assembly 28.

The external catheter tube 22 may be made of a rubber or plastic material which is flexible and soft and yet will not readily twist to stop the flow of urine from the catheter. A main portion 30 of the catheter tube is sized to fit over the penis without causing any constriction and discomfort to the user thereby permitting the penis to assume its normal position. Discomfort to the user is avoided whether the patient is lying in a bed or standing fully clothed. The lower end of the catheter tube is of small diameter and may be connected to a conventional receptacle or the like as desired. The opposite end of the external catheter tube forms the base 34 of the main portion 30 and may include an enlarged bead 36 at the free edge to reinforce the base 34. The bead 36 prevents tears when the catheter tube is being assembled or disassembled and provides a positive grip during assembly.

The cylindrical belt receptacle 24 includes an inwardly tapered inner cylindrical wall 38 which has an outside diameter, over at least a portion of its length, which is larger than the inside diameter of the base 34 of the external catheter tube 22. The external catheter tube may then be stretched when it is extended over the inner cylindrical wall 38 as shown in FIG. 3. An inwardly tapered cylindrical outer wall 40 is connected at its smaller diameter end by a radial wall 42 to the larger diameter end of the inner cylindrical wall 38 to form a cup recess 44 around the inner cylindrical wall 38.

The belt assembly 28 includes a waist belt 46, which extends around the patient's waist as shown in FIG. 2, and a conventional buckle and adjusting device 48 to permit adjustment of the belt to the waist size of the patient and to permit removal of the belt from the waist of the patient. Two abdominal straps 50 loop over the waist belt 46 at the sides of the patient, as shown in FIG. 2, and have turnover buckles 52 at the looped ends to permit the desired adjustment of length depending on the size of the patient. The free ends of the abdominal straps extend into the cup recess 44 adjacent the outer wall 40 of the belt receptacle. A central strap 54 similar to the abdominal straps 50 extends around the waist belt at the center of the patient's waist with its free end similarly extending into the cup recess 44. Legs straps 56 extend from the cup recess 44, similar to abdominal straps 50 and central strap 54, and have looped ends formed by turnover buckles 58 with the loops extending around the abdominal straps 50 as shown in FIG. 2 to provide a comfortable support for the cylindrical belt receptacle 24.

The free ends of the abdominal straps 50, central strap 54 and leg straps 56 are retained in the cup recess 44 by the belt retaining ring 26 which includes a cylindrical ring portion 60 which fits into the cup recess 44. The cylindrical ring portion 60 compresses the free ends of the straps against the outer wall 40, as shown in FIGS. 3 and 4, while the inner surface of the cylindrical ring portion may include ribs 62, as shown in FIGS. 3 and 4, which compress the bead 36 of the external catheter tube 22 against the inner cylindrical wall 38. The outer end of the cylindrical ring portion 60 includes a radial flange 64 which covers the cup recess 44 and improves the appearance and sanitation of the device.

To assemble the catheter device, the external catheter tube 22 is rolled or slipped over the tapered cylindrical inner wall 38 to the position shown in FIG. 3. The free ends of the straps 50, 54 and 56 are positioned adjacent the outer wall 40 of the cylindrical belt receptacle 24 and the belt retaining ring 26 is pressed into the locking position shown in FIG. 3. The belt retaining ring 26 retains the straps in the desired orientation, as shown in FIG. 4, and prevents the external catheter tube from sliding off the inner wall 38. The abdominal straps 52 and the center strap 54 are looped around the waist strap 46, as shown in FIG. 1, and the leg straps 56 are looped around the abdominal straps 50, as shown in FIGS. 1 and 2. The patient, if he is ambulatory, may then step into the device and have the straps adjusted, as shown in FIG. 2, to compress the cylindrical belt receptacle 24 against the pubis of the patient to thereby prevent the leakage of urine from the catheter tube.

If the patient is not ambulatory, the straps may be positioned on a patient's body, as shown in FIG. 2, with the cylindrical belt receptacle 24 positioned around the penis and the free ends of the straps extending into the cup recess 44. The belt retaining ring 26 is then pressed into the position shown in FIG. 3 thereby positioning the external catheter device on the patient without requiring any movement by the patient. The reverse of this process is followed for removal and inspection of the various components.

From the foregoing detailed description, it will be evident that there are a number of changes, adaptations and modifications of the present invention which come within the province of those skilled in the art. However, it is intended that all such variations not departing from the spirit of the invention be considered as within the scope thereof and limited solely by the appended claims.

I claim:

1. An external male catheter device comprising a flexible catheter tube sized to surround the male organ and having a drainage end for connection to a receptacle or the like and a base end, a cylindrical belt receptacle over which the base end of the catheter tube is stretched, said receptacle having a concentric recess around the base thereof, support straps for extending around portions of the patient and having first and second ends with said first ends extending into said concentric recess, and a belt retaining ring sized to fit into the cup recess and compress portions of the first ends of the support bands against the belt receptacle to retain the catheter tube and support straps in a desired position thereby providing an external catheter which is easily removed and disassembled for cleaning and inspection.

2. The catheter of claim 1 wherein the cylindrical belt receptacle has an inner cylindrical wall and an outer cylindrical wall connected by a radial wall to form the cup recess and the inner cylinder wall has an outside diameter which is larger than the inside diameter of the base end of the catheter tube thereby causing the catheter tube to be stretched when the base end is positioned over the inner wall.

3. The catheter of claim 2 wherein the belt retaining ring includes a ring cylindrical wall, which fits into the cup recess, with a radial flange at the outer end of the ring wall with the radial flange extending between the inner wall and the outer wall of the cylindrical belt receptacle.

4. The belt retaining ring of claim 3 wherein the ring cylindrical wall includes ribs on the inner surface of the wall to engage the base of the catheter tube and press the base against the inner wall of the cylindrical belt receptacle.

5. The catheter device of claim 1 additionally including a waistband which may be positioned around the waist of the patient and wherein the support straps include two abdominal straps having said second ends connected to the waistband, said support straps additionally including two leg straps with said second ends connected to said abdominal straps thereby permitting the leg straps to extend around the inside of the patient's legs.

6. The catheter device of claim 5 wherein the connections between the two abdominal straps and the waistband are loops at the second ends of the abdominal straps with said loops extending around the waistband, wherein the connections between the leg straps and the abdominal straps are loops at the second ends of the leg straps with said loops extending around the abdominal straps and wherein the straps and waistband are adjustable in length thereby providing a catheter device which can be fitted to patients of different size.

* * * * *